United States Patent [19]
Staubli

[11] Patent Number: 5,193,999
[45] Date of Patent: Mar. 16, 1993

[54] ABUTMENT SELECTOR

[75] Inventor: Peter E. Staubli, San Carlos, Calif.

[73] Assignee: Attachments International, Inc., San Mateo, Calif.

[21] Appl. No.: 791,726

[22] Filed: Nov. 14, 1991

[51] Int. Cl.⁵ .............................................. A61C 19/04
[52] U.S. Cl. ........................................ 433/72; 33/514
[58] Field of Search ................ 433/72, 75; 33/513, 33/514

[56] References Cited

U.S. PATENT DOCUMENTS

| | | | |
|---|---|---|---|
| 904,990 | 11/1908 | Powers | 433/102 |
| 1,061,398 | 5/1913 | Newman | 33/514 |
| 1,586,302 | 5/1926 | Funk | 433/141 |
| 2,552,134 | 5/1951 | Berliner | 433/143 |
| 3,094,115 | 6/1963 | Polin | 433/72 |
| 3,388,473 | 6/1968 | Loran | 433/75 |
| 3,411,723 | 11/1968 | Kohn | 241/168 |
| 3,559,292 | 2/1971 | Weissman | 33/514 |
| 3,935,640 | 2/1976 | Cohan | 433/75 |
| 4,252,522 | 2/1981 | Petty et al. | 433/75 |
| 4,340,069 | 7/1982 | Yeaple | 128/776 |
| 4,364,730 | 12/1982 | Axelsson | 433/141 |
| 4,768,952 | 9/1988 | Loewenthal | 433/72 |
| 4,886,454 | 12/1989 | Lowenthal | 433/72 |
| 5,035,616 | 7/1991 | Woelfel | 433/72 |

*Primary Examiner*—John J. Wilson
*Attorney, Agent, or Firm*—Townsend and Townsend

[57] ABSTRACT

A method and apparatus for measuring the distance between the gum tissue surface to the implant, along a nonlinear surface, the height needed for determining correct abutment size. The abutment measurement device is an elongated cylindrical member or handle which terminates at both ends with a probe tip. A first probe extends from one end of the elongated member at approximately an 80 degree angle from the member axis. A second probe extends from the other end of the elongated member. The cross section of the second probe tip has a circular cross-section with a concave indentation. This concave indentation is designed to fit the curvature of the sidewall of a secondary healing cap. The concave indentation of the probe tip allows a more accurate measurement of the gum tissue depth.

13 Claims, 2 Drawing Sheets

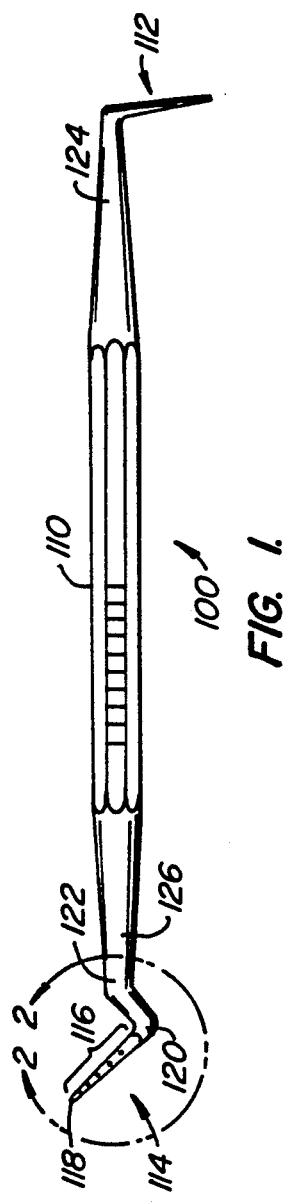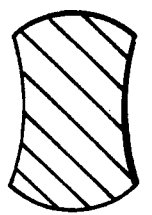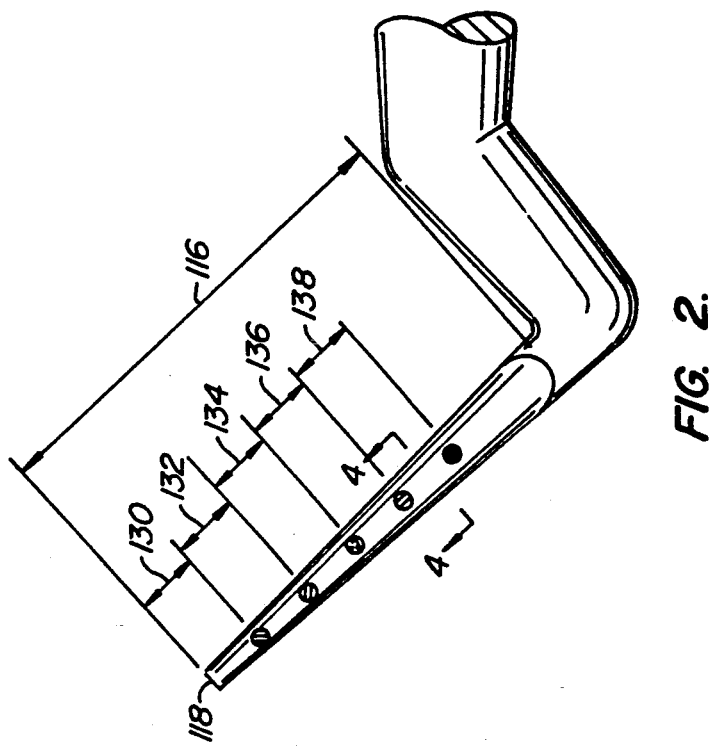

ABUTMENT SELECTOR

BACKGROUND OF THE INVENTION

This invention relates generally to dental measurement instruments and more particularly to a dental probe for measuring the distance from the gum tissue surface to the jawbone which is supporting an implant.

When a tooth has severe nerve damage or is totally edentulous, a dentist will often replace the damaged tooth with an implant. In preparing the patient for receipt of an implant, an insert is positioned into the jawbone. Placing the insert inside the bone involves cutting the gum tissue above the area where the implant will be placed, drilling into the jawbone, and screwing the insert into the jawbone. Typically, a secondary healing cap is placed over the insert to maintain the opening through the gum tissue. The secondary healing cap allows gum tissue to heal until prosthetic fabrication can be completed.

After the gum tissue heals, the surgeon will replace the secondary healing cap with an abutment. The abutment is typically a circular structure which screws into the implant. The abutment radius is approximately the same radius as the secondary healing cap. The abutment height should equal the distance between the gum tissue surface and the jawbone.

Because the height of the gum tissue varies depending on the individual patient and upon the position in the patient's mouth, abutment size must also vary. The abutment size refers to the height of the abutment. Standard abutments come in sizes which vary in 1.0 millimeter (0.039 inch) increments. Thus a dentist may choose a 2.0 millimeter or 3.0 millimeter abutment, but not a 2.5 millimeter abutment.

Most dentists simply guess the height of the patient's gum tissue in size trying to determine the correct abutment size. Other dentists try to obtain a more accurate measurement by using currently available dental probes to measure gum tissue height. Using currently available dental probes is problematic since they are typically not designed to measure the distance from the gum tissue surface to the jawbone. For example, U.S. Pat. Nos. 4,340,069, 4,364,730, and 4,768,952 disclose dental probes designed to measure the height of a periodontal cavity, and in particular, how far the periodontal cavity extends beyond the boundary between the tooth enamel and the root cementum. U.S. Pat. No. 1,586,302 discloses a specialized dental probe designed to dispense medication into a periodontal cavity. U.S. Pat. Nos. 3,559,292, 904,990 and 3,388,473 disclose dental probes designed for probing and measuring the distance of the cavity inside the tooth and its root canal.

Using the aforementioned dental probes for measuring the gum tissue height to determine the correct abutment size is often difficult and sometimes inaccurate. One problem with currently available dental probes is that the probe tips are typically circular in cross section. In measuring the gum tissue height, the tip of the dental probe is inserted in the juncture between the gum tissue and the secondary healing cap. Thus, the gum tissue height is measured on the side of the probe tip furthest away from the secondary healing cap. Since the distance between the tip of the probe and the wall of the secondary healing cap is equal to the radius of the probe at its widest point, the measurement of gum tissue height is not made at the exact location where the abutment is to be placed, but at a location which is a probe tip circumference away from the secondary healing cap. Furthermore, because the probe tip is circular, the curvature of the probe tip does not fit the curvature of the secondary healing cap sidewalls. Thus the probe tip is prone to slippage or misalignment which can lead to inaccuracies in measurement.

Another problem with using currently available dental probes is inaccuracy caused by gum tissue movement. Inserting the probe tip into the juncture between the secondary healing cap and gum tissue displaces gum tissue. Because the secondary healing cap is firmly implanted into the jaw bone, tissue movement next to the probe tip causes gum tissue to bunch up around the probe tip increasing gum tissue height. An increase gum tissue height measurement leads to inaccurate abutment height measurement.

Using currently available dental probes to measure gum tissue height is difficult, thus making selection of an incorrect abutment size likely. Choosing the wrong abutment size increases the time spent on and the expense associated with the abutment placement or replacement procedure. Considerable time is added to the procedure since the dentist must take the time necessary to redo the procedure. The dentist must remove the incorrectly sized abutment, remeasure a new abutment, and put on a new abutment. In addition, material costs are increased. The incorrectly sized abutment must either be thrown away, adding to material costs, or resterilized to be used in another patient procedure. An alternative method of determining the correct abutment size is needed.

SUMMARY OF THE INVENTION

The present invention provides a method and apparatus for measuring the distance along a nonlinear surface from the gum tissue surface to the jawbone, the height needed for determining a correct abutment size. The abutment measurement device is an elongated cylindrical member serving as a handle which terminates at both ends with a probe tip. A first probe tip extends from one end of the elongated member at approximately an 80 degree angle from the member axis. A second probe tip extends from the other end of the elongated member. The second probe tip is a tapered rod of a generally circular in cross section with a concave indentation along the length of the rod. The concave indentation is designed to fit the curvature of a secondary healing cap mounted on the implant.

The concave indentation in the probe tip allows for a more accurate measurement of the gum tissue depth. First, the probe tip is more likely to have the proper alignment without slippage. Second, because the indented probe tip fits along the side of the secondary healing cap, there is less tissue displacement and therefore decrease stress to the surrounding gum tissue. Decreased gum tissue movement reduces inflammation and improves the measurement accuracy. When gum tissue is displaced it bunches up, thus increasing the height of the gum tissue adjacent to the dental probe.

A further understanding of the nature and advantages of the invention may be realized by reference to the remaining portions of the specification and the drawings.

BRIEF DESCRIPTION OF THE DRAWINGS

FIG. 1 is a side plane view of the abutment selector according to the preferred embodiment of the present invention.

FIG. 2 is a magnified side plane view of the probe tip of the abutment selector according to the present invention.

FIG. 4 is a cross-sectional view of the probe tip of the abutment selector according to the present invention.

FIG. 5 is a cross-sectional view of an alternative embodiment of the probe tip of the abutment selector according to the present invention.

FIG. 6 is a cross-sectional view of an alternative embodiment of the probe tip of the abutment selector according to the present invention.

FIG. 7 is a cross-sectional view of an alternative embodiment of the probe tip of the abutment selector according to the present invention.

DESCRIPTION OF THE PREFERRED EMBODIMENT

Figure 8:
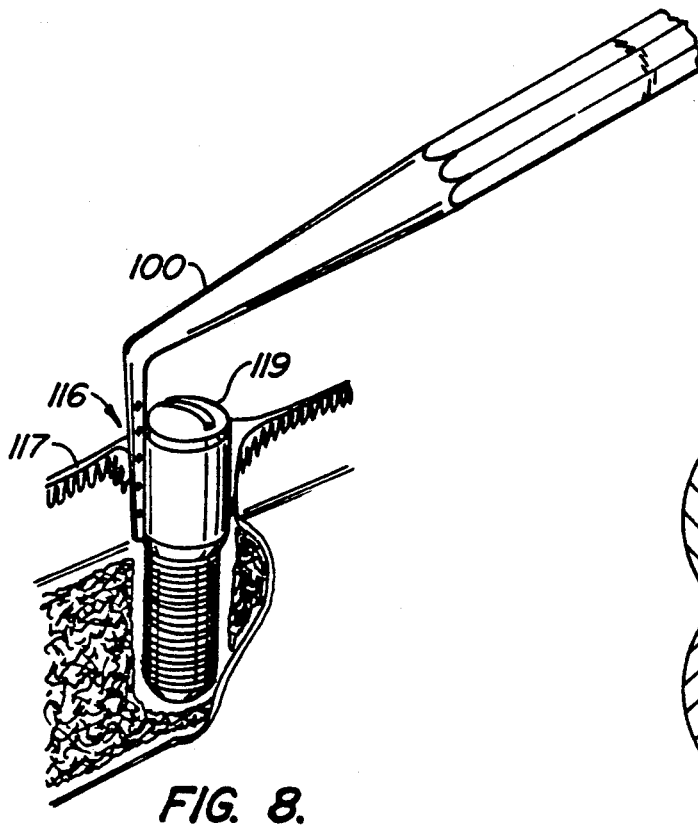
FIG. 8 is a perspective view of the abutment selector according to the present invention inserted at the junction between the secondary healing cap and the gum tissue.

FIG. 1 illustrates an abutment selector 100 which is comprises an elongated member 110 used as a handle or gripping surface, and two probing members 112 and 114. The abutment selector 100 is probably made of an FDA approved non-toxic plastic material, but alternatively may be made of a metallic compound. The first probing member 114 has a first portion 116, which is disposed between a tip 118 and a first bend 120. The elongated member 110 has a second bend 122 disposed between the first bend 120 and a distal end 126.

The elongated member 110 may have any number of bends at any desired angle to achieve the desired functions of enabling the dental probe to be held by the hand and enabling the easy insertion of the distal end 126 into the seam between the secondary healing cap and the gum tissue. The purpose of the bends in the elongated member 110 is to offset the distal end 126 at an angle which facilitates easy insertion and examination of the abutment selector distance markings. In the preferred embodiment of the present invention, the second bend 122 is directed at an obtuse angle from a first side of the elongated member 110. The first bend 120 is directed at an obtuse angle from a second side opposite the first side of the elongated member 110.

FIG. 2 shows a magnified cross-sectional view of one embodiment of the abutment selector probing member 114 shown in FIG. 1. The first portion 116 is approximately 0.546 inches in length and is used for measuring the desired height of the selected abutment. The first portion 116 is generally circular in form exclusive of nonlinear or concave indentations which follow the curvature of the secondary healing cap. The nonlinear indention may be a surface forming an arc which extends parallel to the axis of the probing member. The first portion 116 decreases in circumference terminating in a probe tip 118. The probe tip 118 has a diameter of approximately 0.024 inches. The diameter at the base of the first section 116 of the probing member is approximately 0.074 inches.

Figure 3:
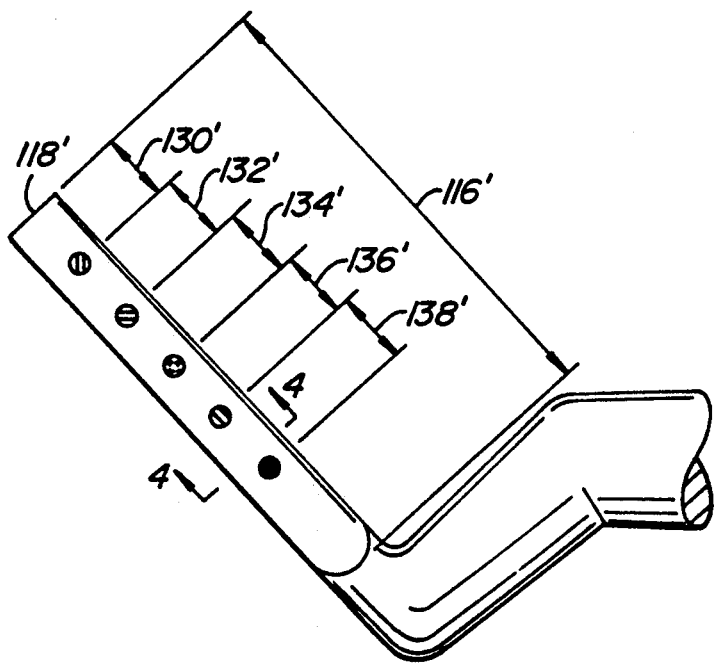
FIG. 3 is a magnified side plane view of the probe tip of the abutment selector according to an alternative embodiment of the present invention.

An alternative embodiment is shown in FIG. 3. Instead of having a probing tip essentially circular in cross-section, the probe tip of the abutment selector forms a shovel having a cross-section which is essentially a rectangle with bowed ends as illustrated in FIG. 6. The first portion 116 of the embodiment illustrated in FIGS. 3 and 6 has a first and second curvilinear surface, where each point on the first surface is equidistant from the second surface. The curvilinear surface fits the curvature of the secondary healing cap.

FIGS. 3 and 4 show cross-sectional views of alternative embodiments of a probe tip 116 which is approximately circular in cross-section. FIGS. 5 and 6 show cross-sectional views of alternative embodiments of a probe tip which is approximately rectangular in cross-section. Although only one side of the illustrated probe tip may be used for gum tissue height measurements, less tissue displacement occurs than in the embodiment shown in FIGS. 3 and 4.

Referring to FIG. 8, the first portion 116 of the abutment selector 100 is inserted in the seam between the gum tissue 117 and the secondary healing cap 119. In one embodiment the abutment selector 100 is demarcated by lines or dots into segments which aid the user in determining the measurement of the gum tissue height. In an alternative embodiment the segments are color coded. Referring to the embodiment shown in FIGS. 2 and 3, the first portion 116 is divided into 0.078 inch color coded segments. Each 0.078 inch segment is color coded with a different color. By noting the color shown above the gum tissue, the dentist can easily determine the gum tissue height.

In the embodiment illustrated in FIG. 2, the distance from the probe tip 118 to a distance 0.078 inch along the first portion 116 of the probing member is color coded red. The second 0.078 inch segment 132 is color coded blue, the third segment 134 is color coded yellow, a fourth segment 136 is color coded green, and a fifth segment 138 is color coded black. Alternatively, different 0.078 inch segments may be marked by a solid line.

When using the abutment selector 100 to make gum tissue measurement, the dentist inserts the abutment selector 100 into the seam between the gum tissue 117 and the secondary healing cap 119 as illustrated in FIG. 8. FIG. 8 illustrates a cross-sectional view of the probe tip and the secondary healing cap according to the present invention, where the first portion 116 of the abutment selector 100 is inserted at the junction between the secondary healing cap 119 and the gum tissue 117. In taking an accurate measurement of the gum tissue height, the dentist should insert the first portion 116 of the abutment selector 100 such that the curved indentation 140 or 142 is aligned with the curvature of the secondary healing cap 119. This positioning allows an accurate measurement of the gum tissue height with both decreased risk of slippage and minimum tissue displacement.

Figure 10:
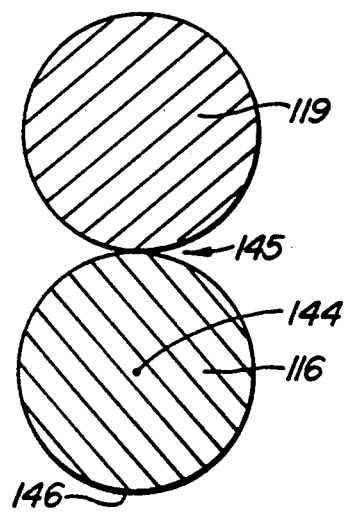
FIG. 10 is a cross-sectional view of the probe tip a prior art dental probe inserted at the junction between the secondary healing cap and the gum tissue.

FIG. 10 illustrates a cross-sectional view of the secondary healing cap 119 and the circular probe tip of a prior art dental probe, where the probe tip is inserted at the seam between the secondary healing cap 119 and the gum tissue 117. The location of the tip of the probe 118 is indicated by the position 144. Because the first portion 116 is circular, the first portion 116 does not fit the curvature of the secondary healing cap 119. The distance between the tip of the probe 118 and the sidewall 145 of the secondary healing cap 119 is equal to the radius of the first portion 116 at its widest point. Because the gum tissue is measured on the side of the probe tip 146 furthest from the secondary healing cap 119, the gum tissue height measurement will be made at location 146 (a circumference away from the sidewall of secondary healing cap).

Displacing gum tissue by a distance equal to the circumference of the probe tip sometimes causes bunching of the gum tissue. This bunching increases the height of the gum tissue next to the measurement probe tip making the dentist guess at the height of gum tissue. The probe tip shown in FIG. 9 increases the accuracy of gum tissue measurement. First, the concave indentation 140, 142 of the first portion 116 has greater surface contact with the secondary healing cap 119 than the probe tip illustrated in FIG. 10. This greater surface contact decreases the likelihood of movement of the probe tip while the dentist is trying to make an accurate measurement. Furthermore, because the concave indentation 140, 142 of the first portion 116 fits the curvature of the secondary healing cap 119, the first portion 116 is more likely to be aligned parallel to the secondary healing cap 119 then the probe tip illustrated in FIG. 10. Because the dentist must visually align the probe tip shown in FIG. 10, the probe tip may be angled and thus not be sufficiently parallel to the sides of the secondary healing cap to get an accurate measurement. A dental probe tip not parallel to the secondary healing cap may increase the gum tissue height measurement leading to an inaccurate measurement.

Figure 9:
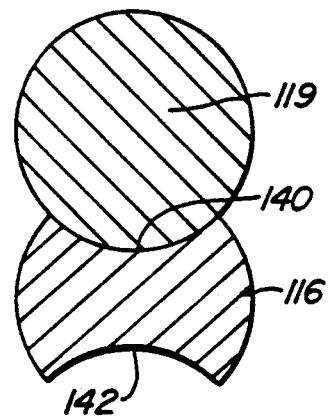
FIG. 9 is a cross-sectional view of the probe tip of the present invention inserted at the junction between the secondary healing cap and the gum tissue.

Because the abutment selector 100 shown in FIG. 8 has concave indentations along its axis of measurement, the insertion of the first portion 116 at the seam between the secondary healing cap 119 causes less tissue displacement then the prior art probe tip illustrated in FIG. 10. The gum tissue height measurement will be taken at a distance approximately equal to the width of the probe tip. Because the width of the probe tip illustrated in FIG. 9 is less than the width of the probe tip illustrated in FIG. 10, the gum tissue height measurement is made closer to the sidewall of the secondary healing cap 119. Furthermore, there is less bunching of gum tissue, leading to a more accurate measurement. Also, less tissue movement decreases the probability of gum inflammation.

The cross-sectional drawings of the probe tips illustrated in FIGS. 4 and 5 show concave indentations on more than one side of the probe tip. Indentations on alternate sides of the abutment selector aid the dentist in making gum tissue measurements. Instead of having to change dental instruments, the dentist may simply change the side of the dental probe tip which is in contact with the secondary healing cap.

As will be understood by the those familiar with the art, the present invention may be embodied in other specific forms without departing from the spirit or essential characteristics thereof. For example, the probe tip indentation may have an oval shaped nonlinear indentation. Accordingly the disclosure of the preferred embodiment of the invention is intended to be illustrative, but not limiting, the scope of the invention which is set forth in the following claims.

What is claimed is:

1. A dental measurement instrument for measuring gum tissue height along a nonlinear surface, comprising:
    an elongated member for providing a gripping surface, said elongated member having an axis; and
    a first portion extending outwardly at an angle from said elongated member, said first portion having a probing member,
    said probing member forming a tip whose perpendicular cross section to the longitudinal axis of said probing member forms a closed figure, said closed figure including at least one nonlinear indentation extending parallel to said longitudinal axis of said probing member, wherein said nonlinear indentation is for conforming to said nonlinear surface, said probing member having measurement segments for measuring said nonlinear surface.

2. The dental measurement instrument according to claim 1 wherein said probing member has a plurality of nonlinear indentations.

3. The dental measurement instrument according to claim 2 wherein said plurality of indentations each conform to different sides of said nonlinear surface.

4. The dental measurement instrument according to claim 1 wherein said nonlinear indentation of said probing member aligns with said probing member so that the axis of said probing member is parallel with the surface of said nonlinear surface.

5. The dental measurement instrument according to claim 1 wherein said nonlinear indentation is concave in form.

6. The dental measurement instrument according to claim 1 wherein said nonlinear surface is a secondary healing cap.

7. The dental measurement instrument according to claim 1 wherein said measurement segments are color coded.

8. The dental measurement instrument according to claim 1 wherein said measurement segments are demarcated by a line.

9. The dental measurement instrument according to claim 1 wherein aid measurement segments are demarcated by dot.

10. The dental measurement instrument according to claim 1 wherein a cross-section of said probing member tip is approximately circular in diameter exclusive of said nonlinear indentation.

11. The dental measurement instrument according to claim 1 wherein a cross-section of said probing member is approximately rectangular in cross-section exclusive of said nonlinear indentation.

12. A dental measurement instrument for measuring gum tissue height along a nonlinear surface, comprising:
    an elongated member for providing a gripping surface, said elongated member having an axis; and
    a first portion extending outwardly at an angle from said elongated member, said first portion having a probing member,
    said probing member forming a tip, wherein the cross section of said probing member forms a closed figure, said closed figure including at least one nonlinear indentation extending parallel to an axis of said probing member, said probing member having measurement segments for measuring said nonlinear surface, said probing member having a first and second curvilinear surface, each point on said first surface being equidistant from said second surface, said first curvilinear surface forming a nonlinear indentation is for conforming to said nonlinear surface.

13. A dental measurement instrument for measuring gum tissue height along a nonlinear surface, comprising:
an elongated member for providing a gripping surface, said elongated member having an axis; and
a first portion extending outwardly at an angle from said elongated member, said first portion having a probing member
forming a tip whose perpendicular cross-section to the longitudinal axis of said probing member forms a closed figure, said closed figure including at least one nonlinear indentation extending parallel to said axis of said probing member, wherein the surface formed by said nonlinear indentation corresponds to said nonlinear surface, the surface of said nonlinear indentation being aligned with said probing member such that the axis of said probing member is parallel to the surface of said nonlinear surface, said probing member having measurement segments for measuring said nonlinear surface.

* * * * *